United States Patent
Koh

(10) Patent No.: US 7,269,459 B1
(45) Date of Patent: Sep. 11, 2007

(54) IMPLANTABLE CARDIAC DEVICE WITH SELECTABLE TIERED SLEEP APNEA THERAPIES AND METHOD

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 374 days.

(21) Appl. No.: 11/054,082

(22) Filed: Feb. 8, 2005

(51) Int. Cl.
*A61N 1/365* (2006.01)

(52) U.S. Cl. ............... 607/20; 607/18; 607/2

(58) Field of Classification Search ............ None
See application file for complete search history.

(56) References Cited

U.S. PATENT DOCUMENTS

| | | | |
|---|---|---|---|
| 5,146,918 A | 9/1992 | Kallok et al. ........... 128/419 G |
| 6,126,611 A * | 10/2000 | Bourgeois et al. .......... 600/529 |
| 2003/0153953 A1 * | 8/2003 | Park et al. .................... 607/17 |
| 2003/0153954 A1 * | 8/2003 | Park et al. .................... 607/17 |
| 2003/0153955 A1 * | 8/2003 | Park et al. .................... 607/17 |
| 2003/0153956 A1 * | 8/2003 | Park et al. .................... 607/17 |
| 2003/0195571 A1 | 10/2003 | Burnes et al. ................. 607/9 |
| 2003/0216789 A1 | 11/2003 | Deem et al. ................... 607/9 |
| 2003/0216790 A1 * | 11/2003 | Hill et al. ...................... 607/17 |
| 2004/0088015 A1 * | 5/2004 | Casavant et al. ............. 607/14 |
| 2005/0065563 A1 * | 3/2005 | Scheiner ........................ 607/9 |
| 2005/0101833 A1 * | 5/2005 | Hsu et al. ..................... 600/26 |

FOREIGN PATENT DOCUMENTS

| | | |
|---|---|---|
| WO | WO 03/096882 A2 | 11/2003 |
| WO | WO 03/096882 A3 | 11/2003 |

* cited by examiner

*Primary Examiner*—Kristen Droesch Mullen

(57) ABSTRACT

An implantable cardiac stimulation device treats apnea with either phrenic nerve stimulation pulses or cardiac stimulation pulses. The device includes an apnea detector that detects apnea of a patient, a blood oxygen saturation monitor that measures a blood oxygen saturation level of the patient responsive to detection of apnea, and a tiered therapy circuit that provides phrenic nerve stimulation pulses if the measured blood oxygen saturation level is within a first range and cardiac stimulation pulses if the measured blood oxygen saturation level is within a second range. The cardiac stimulation pulses are preferably provided in a DAO pacing mode.

20 Claims, 3 Drawing Sheets

IMPLANTABLE CARDIAC DEVICE WITH SELECTABLE TIERED SLEEP APNEA THERAPIES AND METHOD

FIELD OF THE INVENTION

The present invention generally relates to implantable cardiac devices. The present invention more particularly relates to selectable sleep apnea therapies to be provided by such devices to maintain acceptable blood oxygen saturation levels during sleep apnea episodes.

BACKGROUND OF THE INVENTION

Implantable cardiac devices are well known in the art. They may take the form of an implantable defibrillator (ICD) to treat accelerated rhythms of the heart such as fibrillation, or an implantable pacemaker to maintain the heart rate above a prescribed limit, such as, for example, to treat a bradycardia. Implantable cardiac devices are also known which incorporate both a pacemaker and a defibrillator.

The devices are generally implanted in an upper portion of the left-side of the chest beneath the skin of a patient within what is known as a subcutaneous pocket. The implantable devices generally function in association with one or more electrode-carrying leads which are implanted within the heart. The electrodes are positioned within the heart, for making electrical contact with their designated heart chamber. Conductors within the leads couple the electrodes to the device to enable the device to deliver the desired therapy.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

For defibrillation, one lead may include at least one defibrillation electrode arranged to be positioned in the right ventricle. When fibrillation is detected, a pulse generator delivers a defibrillating shock from the defibrillation electrode in the right ventricle to the device conductive housing to terminate the arrhythmia. Alternatively, a further defibrillation electrode may be positioned in the right atrium or superior vena cava and electrically connected to the right ventricular defibrillation electrode. In this arrangement, the defibrillating shock is delivered from the parallel connected defibrillation electrodes to the conductive housing.

Congestive heart failure (CHF) is a debilitating, end-stage disease in which abnormal function of the heart leads to inadequate blood flow to fulfill the needs of the body's tissues. As CHF progresses, blood pressure increases and interstitial fluid accumulates in the lungs around the heart. The accumulated fluid fills the gas air exchange space in the lungs and prevents proper lung function. Reduced oxygen saturation further aggravates cardiac function with possible infarction. Hence, CHF requires constant monitoring.

Sleep apnea is another condition which may benefit from constant or frequent monitoring. Sleep apnea is a serious, potentially life-threatening condition characterized by brief interruptions of breathing during sleep. In a given night, the number of involuntary pauses in breathing (apneic events) may be as high as twenty to sixty or more per hour. During sleep apnea, blood oxygen saturation levels are reduced which may be especially serious for a patient with CHF.

As is known, CHF disease state may be evaluated through impedance measurements utilizing electrodes implanted in the heart. Such measurements may be carried out by applying a current between a pair of the electrodes and measuring the voltage between those electrodes or another pair of electrodes. Hence, an implanted cardiac stimulation device is well suited for such an application. Sleep apnea may also be monitored in this manner.

Implantable cardiac devices are also well suited for providing sleep apnea therapy. One such therapy is phrenic nerve stimulation (PNS). Here, stimulation pulses from the device's pulse generator are applied to phrenic nerves associated with the diaphragm or to diaphragm muscle itself. Both of these forms of stimulation therapy are included herein as PNS.

Another form of therapy which an implantable cardiac device is well suited to provide is overdrive pacing. Here, stimulation pulses are provided to the heart to increase the cardiac rate and cardiac output. The stimulation pulses may be in accordance with a pacing modality referred to as DAO pacing where both the atrial and ventricles are paced. The atrial pacing rate is above a base rate and a ventricular pacing pulse is provided an escape interval after each atrial pacing pulse. DAO pacing is considered effective at preventing central sleep apnea because the higher cardiac rate will increase cardiac output which in turn will decrease the delay in the respiratory control loop.

DAO pacing will achieve its intended purpose only when a patient's blood saturation is not deteriorated. Without proper ventilation, DAO pacing may actually be deleterious because the heart muscle may be forced by the pacing to consume enough oxygen to diminish oxygen supply to the myocardium. If such a condition were to continue, a myocardial infarction could result which in turn could result in a heart attack. The present invention addresses this and other issues which shall become apparent.

SUMMARY

What is described herein is an implantable cardiac stimulation device comprising an apnea detector that detects apnea of a patient and a blood oxygen saturation monitor that measures a blood oxygen saturation level of the patient responsive to detection of apnea. The device further comprises a therapy circuit that provides phrenic nerve stimulation pulses if the measured blood oxygen saturation level is within a first range and cardiac stimulation pulses if the measured blood oxygen saturation level is within a second range.

The apnea detector may include a respiration detector. The respiration detector may include an impedance monitor.

The therapy circuit may withhold therapy if the measured blood oxygen saturation level is within a third range. The second range may be above the first range and the third range may be above the second range.

The therapy circuit may include a pulse generator that provides the cardiac stimulation pulses in an atrial pacing mode. The atrial pacing mode may be an accelerated rate atrial pacing mode. The accelerated rate atrial pacing mode may be a DAO pacing mode.

The invention further provides an implantable cardiac stimulation device comprising an apnea detector that detects apnea of a patient; and a blood oxygen saturation monitor that measures a blood oxygen saturation level of the patient responsive to detection of apnea. The device further comprises a therapy circuit that provides the patient with phrenic nerve stimulation pulses if the measured blood oxygen saturation level is within a first range and accelerated rate atrial stimulation pulses if the measured blood oxygen saturation level is within a second range, wherein the second range is above the first range.

The invention still further provides a method comprising detecting apnea of a patient, measuring a blood oxygen saturation level of the patient responsive to detection of apnea, and providing phrenic nerve stimulation pulse therapy if the measured blood oxygen saturation level is within a first range and cardiac stimulation pulse therapy if the measured blood oxygen saturation level is within a second range.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
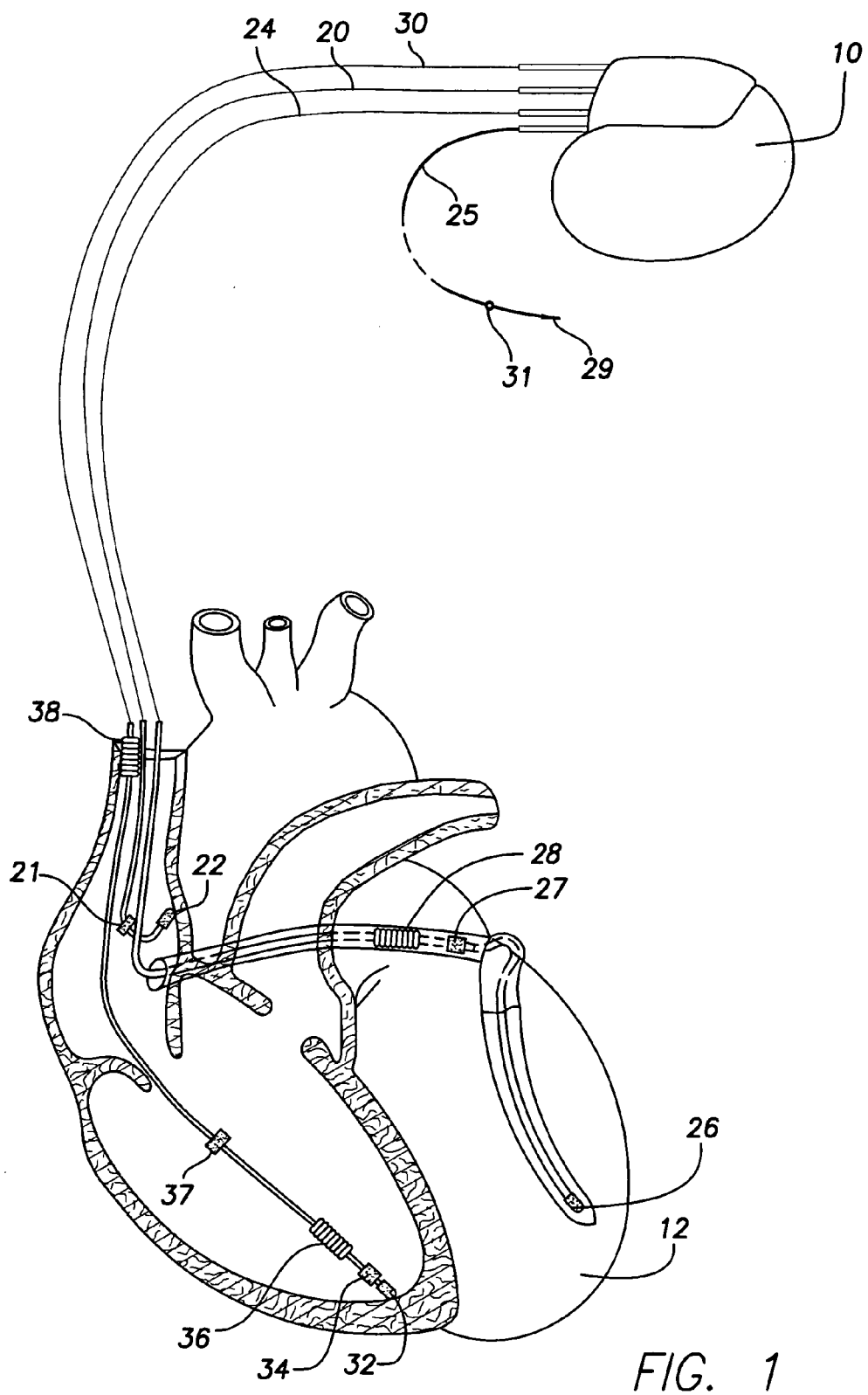
FIG. 1 is a simplified diagram illustrating an implantable cardiac stimulation device embodying the present invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial ring electrode 21 and an atrial tip electrode 22, which are typically implanted in the patient's right atrial appendage. The electrodes 21 and 22 form a bipolar electrode pair useful for right atrial pacing and near field targeted atrial activity sensing.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The device 10 includes a still further lead 25. The lead 25 includes a distal electrode 29 and a proximal electrode 31. The electrodes 31 and 29 may be coupled to the nervous system of the patient for applying phrenic nerve stimulation (PNS) therapy when required and as described hereinafter.

As may be further noted in FIG. 1, the lead 30 further carries a blood oxygen saturation sensor 37. The sensor 37 may be of the type well known in the art which may include an infrared light emitting diode and a photo-electric cell. It senses oxygen saturation levels within the right ventricle and generates a corresponding signal conveyed to the device circuitry through a conductor of lead 30.

Figure 2:
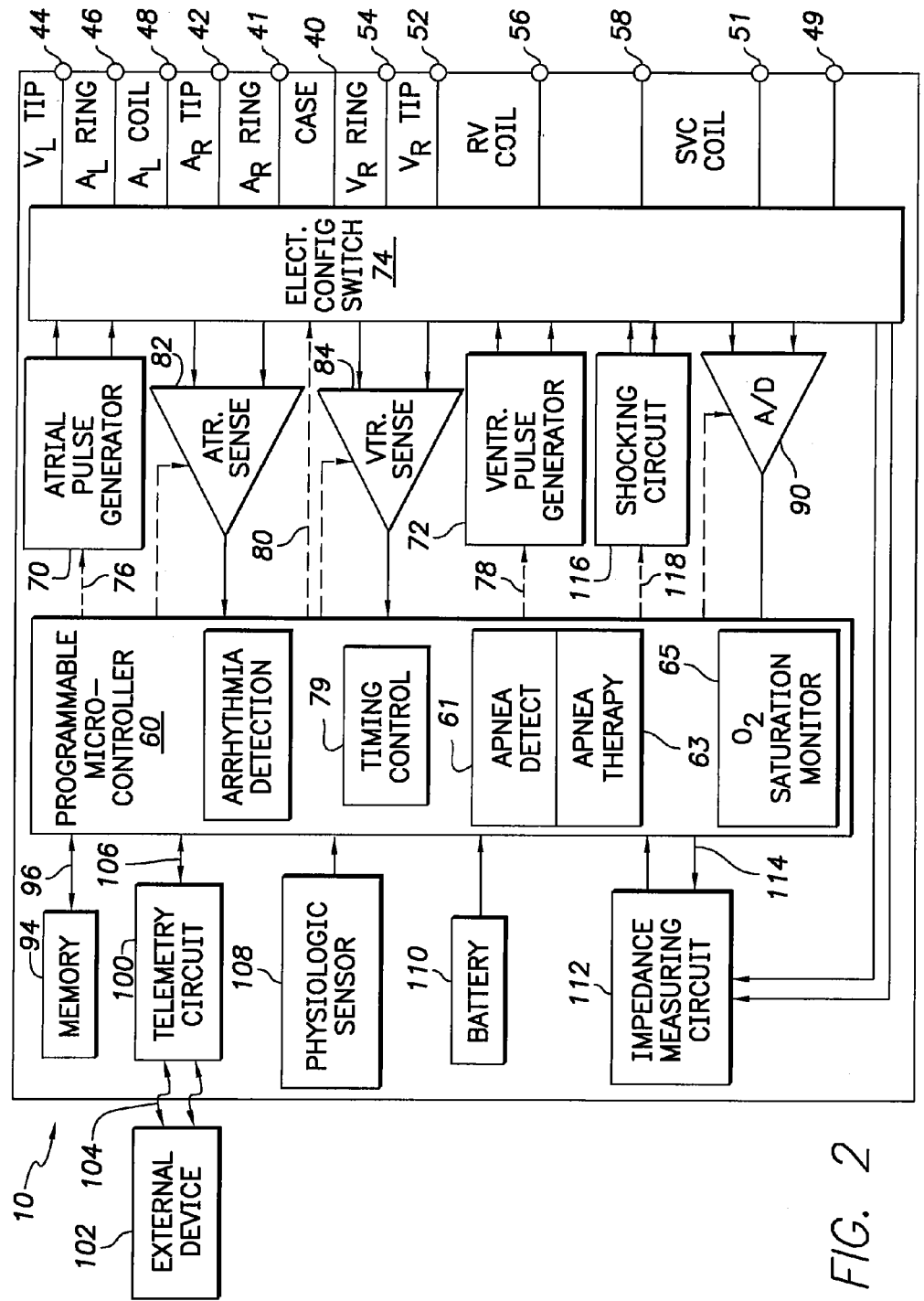
FIG. 2 is a functional block diagram of the implantable cardiac stimulation device of FIG. 1 according to one embodiment of the invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 47, 48, 49, 52, 54, 56, and 58 (shown schematically and, for convenience, the names of the electrodes to which they are connected are shown next to the terminals). As such, to achieve right atrial sensing and pacing, the connector includes at least a right atrial ring terminal ($A_R$ RING) 41 and a right atrial tip terminal ($A_R$ TIP) 42 adapted for connection to the atrial ring and tip electrodes 21 and 22, respectively.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Lastly, to achieve vagal or phrenic nerve stimulation, the electrode 31 may be coupled to terminal 51 and the electrode 29 may be coupled to terminal 49.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74 and PNS pulse for delivery by the PNS lead 25. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of timing periods, as, for example, refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, and according to this embodiment, the device 10 includes an impedance monitor or measuring circuit 112. The measuring circuit 112 is enabled by the microcontroller 60 via a control signal 114. As is known, the impedance measuring monitor 112 may be used for lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. For example, according to this embodiment, the case 40 may serve as one impedance monitoring electrode, and one of electrodes 32, 34, or 36 may be employed as the second impedance monitoring electrode.

More specifically, to measure impedance for detecting sleep apnea, the impedance monitor 112 applies a current between at least two electrodes, as for example among those previously mentioned, and selected by switch 74. As the current is applied, the induced voltage across those electrodes or another electrode pair is sensed. A signal may then be generated representing the respiration of the patient.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As may also be seen in FIG. 2, the device 10 further includes an apnea detector 61, an apnea therapy control 63, and an oxygen saturation monitor 65. The apnea detector 61 utilizes the respiration signal provided by the impedance monitor 112 to detect sleep apnea. For example, the respiration signal will be present during normal breathing. However, during pauses in breathing, such as during apnea, the respiration signal will be at a continuous very low or constant level. The detection of an apnea episode may therefore be accomplished if the respiration signal is continuously low or constant for some predetermined time period. The predetermined time period may be, for example, fifteen seconds. Hence, if the respiration signal indicates a pause in breathing of fifteen seconds, the apnea detection will declare detection of an apnea episode.

Alternatively, the apnea detector 61 may include the oxygen saturation monitor 65 and utilize the oxygen saturation level measured by the monitor 65. When the oxygen saturation level falls below a set limit, sleep apnea may be declared. This allows for continuous monitoring.

When an apnea episode is detected, the oxygen saturation monitor 65 is read for the measured the percentage of blood oxygen saturation. The apnea therapy control 63 may then determine the proper apnea therapy to select. In doing so, the apnea therapy control establishes three different oxygen saturation ranges. A first range may correspond to oxygen saturation levels of less than 70% but greater than zero. A second range may correspond to oxygen saturation levels greater than 70% but less than 80%. A third range may correspond to oxygen saturation levels of greater than 80%. Those ranges are meant to be exemplary only. It should, however, be observed that, the third range is above the second range and the second range is above the first range.

The first range represents the least degree of oxygen saturation. As will be seen subsequently, at these oxygen saturation levels, overdrive pacing could cause excessive depletion of available oxygen which could adversely impact the myocardium. Hence, the apnea therapy to be selected in this case is phrenic nerve stimulation (PNS). Such therapy would serve to increase oxygen saturation without adversely impacting the myocardium. Once O2SAT is recovered to the "middle" range, DAO pacing may be added to the PNS to speed up the recovery from the effect of sleep apnea.

If the measured oxygen saturation level is or rises above 70% into the second range, there is considered sufficient ventilation to support pacing therapy, such as DAO pacing.

If the measured oxygen saturation level is or rises above 80% into the third range, the oxygen saturation will be considered adequate without therapy and all therapy will be terminated or withheld.

Hence, the present invention provides selectable apnea therapy based upon oxygen saturation. Therapy is provided in a manner aimed to improve the oxygen saturation levels while allowing pacing to be a therapy option. When pacing is not employed when therapy is required, PNS is used instead.

Figure 3:
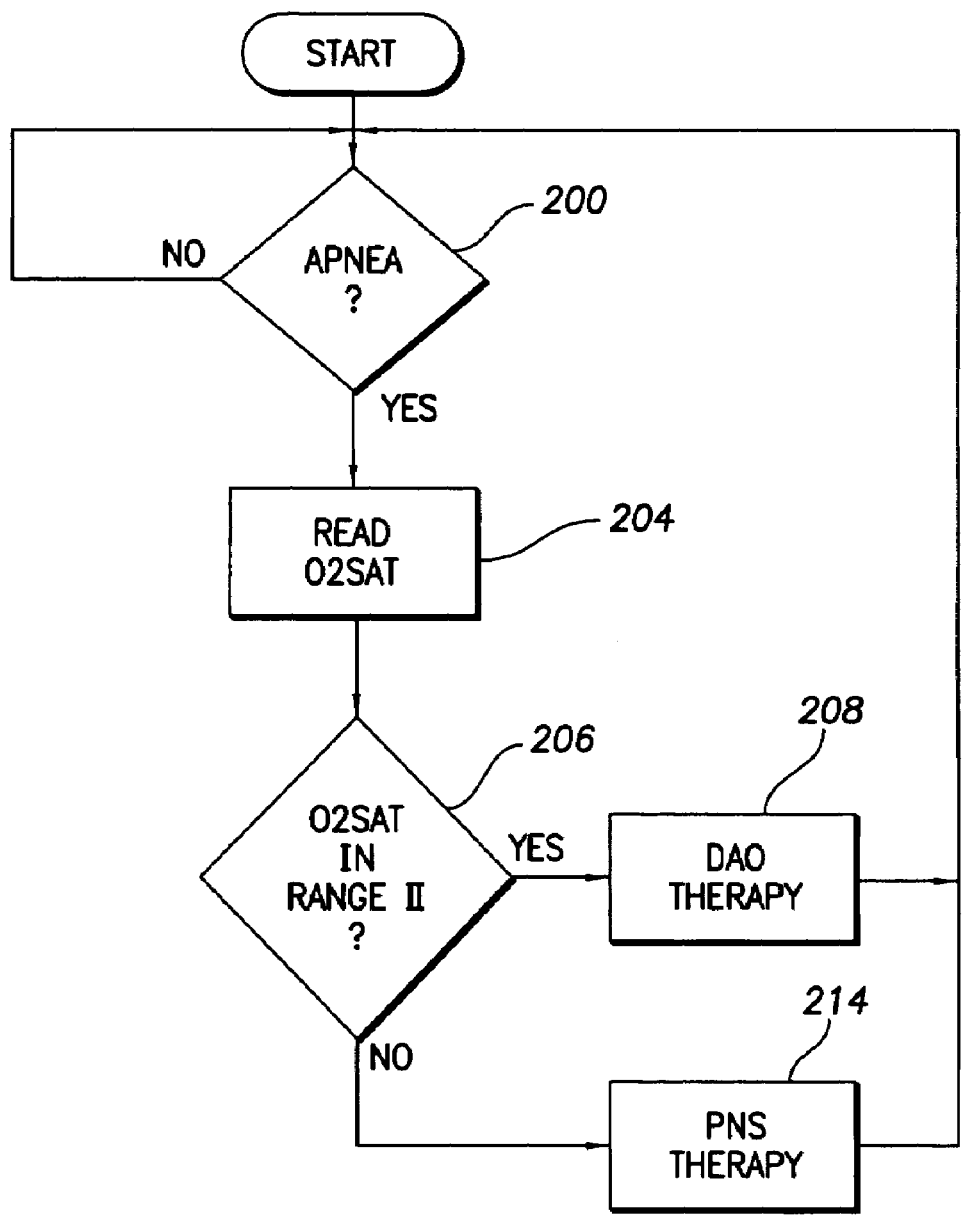
FIG. 3 is a flow diagram describing an overview of one embodiment.

Referring now to FIG. 3, it is a flow chart describing the overview of the operation and novel features implemented in one embodiment of the device 10 in accordance with the present invention. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Referring now to FIG. 3, the process thereshown initiates with decision block 200. In decision block 200, the apnea detector 61 determines if an episode of apnea has begun. When an episode of sleep apnea is detected in accordance with decision block 200, the process advances to activity block 204 wherein the apnea therapy control 63 reads the blood oxygen saturation level measured by the blood oxygen saturation monitor 65. The process then advances to decision block 206 wherein it is determined by the apnea therapy control 63 if the blood oxygen saturation level measured by the saturation monitor 65 is within the second range. If it is, this would indicate that accelerated pacing therapy, such as DAO therapy may be provided to treat the apnea. Accordingly, if the oxygen saturation level is within the second range, the process advances to activity block 208 wherein DAO pacing therapy is administered. The process then returns to decision block 200 for continued apnea monitoring.

If in decision block 206 it is determined that the blood oxygen saturation level measured by the blood oxygen saturation monitor 65 is not within the second range, this means that the measured blood oxygen saturation level is within the first range. Since the blood oxygen saturation level is within the first range, PNS therapy is indicated. Accordingly, the process then advances to activity block 214 wherein PNS therapy is administered. The process then returns to decision block 200 for continued apnea monitoring.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. In an implantable cardiac device, a method comprising:
   detecting apnea of a patient;
   measuring a blood oxygen saturation level of the patient responsive to detection of apnea; and
   selecting one of phrenic nerve stimulation therapy or cardiac stimulation pulse therapy depending upon the blood oxygen saturation level.

2. The method of claim 1, wherein selecting comprises selecting phrenic nerve stimulation therapy if the blood oxygen saturation level is below a threshold value, and cardiac stimulation pulse therapy if the blood oxygen saturation level is above the threshold value.

3. The method of claim 1, wherein providing comprises withholding therapy if the blood oxygen saturation level is above a maximum threshold value.

4. An implantable cardiac stimulation device comprising:
   an apnea detector that detects apnea of a patient;
   a blood oxygen saturation monitor that measures a blood oxygen saturation level of the patient responsive to detection of apnea; and
   a therapy circuit that selects between phrenic nerve stimulation pulses and cardiac stimulation pulses based on the blood oxygen saturation level.

5. The device of claim 4, wherein the apnea detector includes a respiration detector.

6. The device of claim 5, wherein the respiration detector includes an impedance monitor.

7. The device of claim 4, wherein the therapy circuit withholds therapy if the measured blood oxygen saturation level is within a predefined range.

8. The device of claim 7, wherein the predefined range is above a threshold value.

9. The device of claim 4, wherein the therapy circuit includes a pulse generator that provides the cardiac stimulation pulses in a DAO pacing mode.

10. The device of claim 4 wherein the apnea detector includes an oxygen saturation monitor.

11. An implantable cardiac stimulation device comprising:
    an apnea detector that detects apnea of a patient;
    a blood oxygen saturation monitor that measures a blood oxygen saturation level of the patient responsive to detection of apnea; and
    a therapy circuit that provides phrenic nerve stimulation pulses if the measured blood oxygen saturation level is within a first range and cardiac stimulation pulses if the measured blood oxygen saturation level is within a second range, different from the first range.

12. The device of claim 11, wherein the apnea detector includes a respiration detector.

13. The device of claim 12, wherein the respiration detector includes an impedance monitor.

14. The device of claim 11, wherein the second range is above the first range.

15. The device of claim 11, wherein the therapy circuit withholds therapy if the measured blood oxygen saturation level is within a third range.

16. The device of claim 15, wherein the second range is above the first range and wherein the third range is above the second range.

17. The device of claim 11, wherein the therapy circuit includes a pulse generator that provides the cardiac stimulation pulses in an atrial pacing mode.

18. The device of claim 17, wherein the atrial pacing mode is an accelerated rate atrial pacing mode.

19. The device of claim 18, wherein the accelerated rate atrial pacing mode is a DAO pacing mode.

20. The device of claim 11 wherein the apnea detector includes an oxygen saturation monitor.

* * * * *